(12) United States Patent
Haider et al.

(10) Patent No.: US 9,747,653 B2
(45) Date of Patent: Aug. 29, 2017

(54) AUTHENTICATION SYSTEM FOR MOBILE DEVICES FOR EXCHANGING MEDICAL DATA

(71) Applicant: Siemens Aktiengesellschaft, Munich (DE)

(72) Inventors: Sultan Haider, Erlangen (DE); Georg Heidenreich, Erlangen (EA)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 506 days.

(21) Appl. No.: 14/372,794

(22) PCT Filed: Jan. 30, 2013

(86) PCT No.: PCT/EP2013/051799
§ 371 (c)(1),
(2) Date: Jul. 17, 2014

(87) PCT Pub. No.: WO2013/113756
PCT Pub. Date: Aug. 8, 2013

(65) Prior Publication Data
US 2015/0032633 A1   Jan. 29, 2015

(30) Foreign Application Priority Data
Feb. 2, 2012 (DE) .................. 10 2012 201 505

(51) Int. Cl.
*G06F 21/00*  (2013.01)
*G06Q 50/22*  (2012.01)
*G06F 19/00*  (2011.01)
*H04L 29/06*  (2006.01)
*G06Q 10/06*  (2012.01)

(52) U.S. Cl.
CPC .......... *G06Q 50/22* (2013.01); *G06F 19/322* (2013.01); *G06Q 10/06* (2013.01); *H04L 63/0823* (2013.01); *G06Q 2220/10* (2013.01)

(58) Field of Classification Search
CPC .................... G06F 19/322; H04L 63/0823
See application file for complete search history.

(56) References Cited

U.S. PATENT DOCUMENTS

2005/0021937 A1   1/2005 Lambert
2005/0210236 A1   9/2005 Lee et al.
(Continued)

FOREIGN PATENT DOCUMENTS

CN   1860471 A    11/2006
CN   101132281 A   2/2008
(Continued)

OTHER PUBLICATIONS

Chinese Office Action and English translation thereof dated Jun. 3, 2016.
(Continued)

*Primary Examiner* — Morshed Mehedi
(74) *Attorney, Agent, or Firm* — Harness, Dickey & Pierce, P.L.C.

(57) ABSTRACT

An authentication system, a mobile electronic device, an instantiating unit and a method, as well as a computer program product are disclosed for the authentication of a patient against a central registry which exchanges data with a repository for the storage of medical data records. In an embodiment, an individualized application is loaded and installed on the mobile radio device in order to sign messages to the registry with a signature. The signature can be triggered in the registry to check the authenticity of the remote patient in order to provide data access.

29 Claims, 2 Drawing Sheets

(56) References Cited

U.S. PATENT DOCUMENTS

| | | | |
|---|---|---|---|
| 2007/0067833 A1* | 3/2007 | Colnot | H04L 9/3271 726/9 |
| 2007/0074040 A1* | 3/2007 | Lakshmeshwar | G06F 21/32 713/186 |
| 2010/0146085 A1* | 6/2010 | Van Wie | H04L 12/00 709/220 |
| 2010/0257360 A1* | 10/2010 | Bae | H04L 9/0866 713/168 |
| 2010/0257380 A1 | 10/2010 | Bae | |
| 2011/0185397 A1* | 7/2011 | Escott | H04B 7/155 726/3 |
| 2011/0295078 A1 | 12/2011 | Reid et al. | |

FOREIGN PATENT DOCUMENTS

| | | |
|---|---|---|
| CN | 101183938 A | 5/2008 |
| CN | 101296107 A | 10/2008 |
| CN | 102111271 A | 6/2011 |
| DE | 10242673 A1 | 3/2004 |
| WO | WO 2011011454 A1 | 1/2011 |

OTHER PUBLICATIONS

Koufi V. et al; "HDGPortal: A Grid prtal application for pervasive access to process-based healthcare systems"; Pervasive Computing Technologies for Healthcare, 2008. Pervasivehealth 2008. Second International Conference on IEEE, Piscataway, NJ; pp. 121-126; ISBN: 978-963-9799-15-8; XP031289750; 2008; US; Jan. 30, 2008.

International Search Report PCT/ISA/210 for International Application No. PCT/EP2013/051799 Dated Mar. 21, 2013.

Written Opinion of the International Searching Authority PCT/ISA/237 for International Application No. PCT/EP2013/051799 dated Mar. 21, 2013.

German Office Action dated Mar. 12, 2012.

* cited by examiner

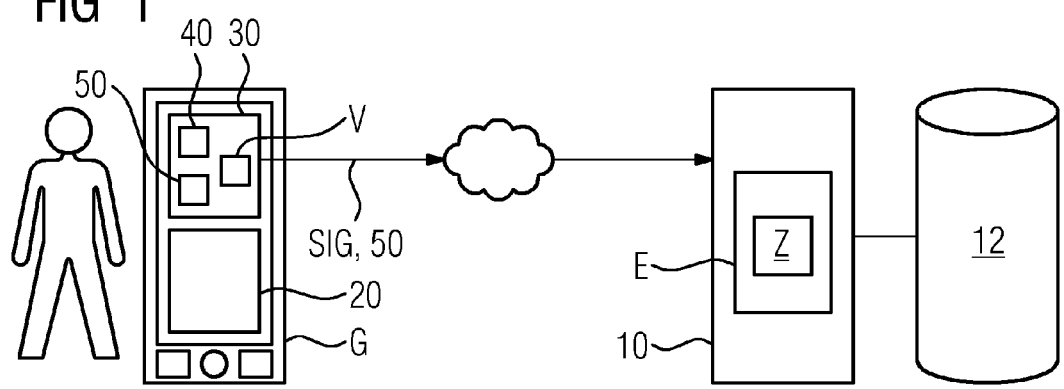
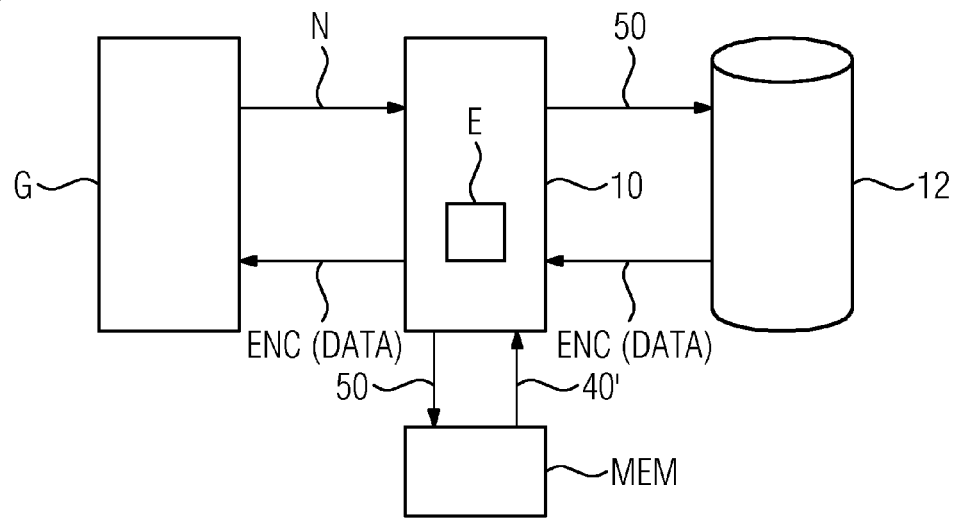
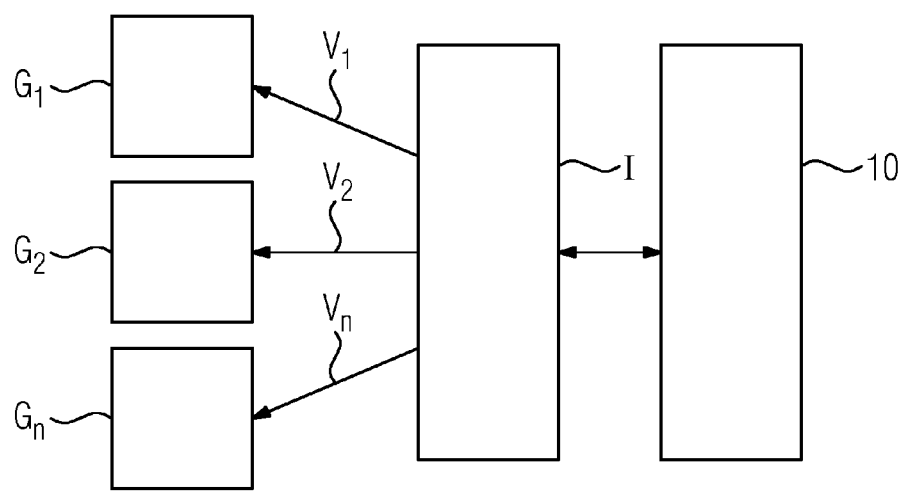

AUTHENTICATION SYSTEM FOR MOBILE DEVICES FOR EXCHANGING MEDICAL DATA

PRIORITY STATEMENT

This application is the national phase under 35 U.S.C. §371 of PCT International Application No. PCT/EP2013/051799 which has an International filing date of Jan. 30, 2013, which designated the United States of America, and which claims priority to German patent application number DE 102012201505.1 filed Feb. 2, 2012, the entire contents of each of which are hereby incorporated herein by reference.

FIELD

At least one embodiment of the present invention generally lies in the fields of medical technology and information technology and generally relates to an authentication system for the authentication of mobile electronic devices against a central server for the secure exchange of medical data.

BACKGROUND

With regard to today's modern medical systems which in the vast majority of cases are used by hospitals the data is available as digital data and is also exchanged in digital form over corresponding networks. In contrast to earlier systems, in which for example in radiology X-ray images of patients were still filed and stored in the form of X-ray films, the radiological image data captured today is captured digitally, further processed digitally and/or forwarded digitally to other entities (also including external entities).

One advantage of digital data processing in medicine can be seen in the extremely simple and flexible manner in which medical data records are forwarded and made available. The data exchange is normally based on a special protocol, for example the DICOM protocol (DICOM: Digital Information and Communication in Medicine).

When a patient has left the hospital again, then under certain circumstances it is also important for him to be able to access his medical image data. This becomes important at times such as when follow-up examinations become necessary for which the already acquired image data or other patient data needs to be available. The data is held in a hospital repository.

There are however also problems associated with the transfer of digital data. It is thus easier for attackers to gain unauthorized access to said data records. In other words, it is essential to protect the digital data against unauthorized access but nevertheless to enable easy accessibility of the data for the patient when doing so. In this situation the IT resources of the computer entities involved should also be taken into consideration (bandwidth, addressing of device components etc.)

Identification and authentication systems are well known in the prior art. Known cryptological procedures are employed as a rule in this situation in order to be able to prove the identity of a user so as to authenticate him against the system.

In particular, in medical systems it is indispensable that secure communication channels can be made available for communication between patient and hospital or clinical data records. In order to give the patient in question the greatest possible degree of flexibility in accessing his clinical data records it is desirable to use mobile electronic devices, such as for example smartphones or mobile telecommunication facilities, which the patient generally has at his disposal in any case. For this purpose it is necessary to store the personal access data on the respective electronic device and transmit it over the known standardized communication channels, such as for example the relevant mobile network operator.

It is obvious that the personal access data can very easily be corrupted or compromised during such a data exchange. The mobile communication connections can be manipulated relatively easily by an attacker in order to tap the access data or other personal data. Additional security measures are therefore required, but there is an associated high administrative effort, in particular on the part of the patient or the mobile device.

Known systems are therefore based on the provision of a security infrastructure, which as a rule is provided by third-party suppliers, so as to be available for the mobile devices. In addition to the high administrative effort, a further disadvantage regarding the known systems in the prior art consists in the fact that the availability of a secure authentication is reduced by the establishment of specific security infrastructures.

SUMMARY

At least one embodiment of the present invention is therefore directed to improving and simplifying the identification and authentication of patients using mobile electronic devices against a central system in which medical data records are stored, wherein the security both for the operator of the mobile device and also for the operator of the central server should simultaneously be improved. At the same time, device components are modified and addressed in a novel fundamentally different manner in order to allow the security of the authentication system to be enhanced.

An authentication system, a mobile electronic device, an instantiating unit, a method for the authentication and a computer program product are disclosed.

Features, advantages and/or alternative embodiments can also be applied to the other claimed matters (and thus to the mobile electronic device, to the instantiating unit and to the computer program product and the method), and vice versa. In other words, the other forms of claims can also be developed by way of the features which are described or claimed in connection with the system. In this situation the corresponding functional features of the system or of the method are implemented by way of appropriate representational modules, in particular by hardware modules or microprocessor chip modules which are implemented on the electronic device or on the instantiating unit. The individual modules or units of the system can basically be implemented as software modules and/or as microprocessor chip modules.

According to one aspect of at least one embodiment, the invention relates to an authentication system for the authentication of a particular mobile electronic device (wherein a plurality of mobile electronic devices is basically connected to the system and is to be authenticated) against a central server for the secure exchange of medical data between device and server, wherein the server for its part exchanges data with a clinical system and has access to a repository containing clinical or medical data (also including patient data), comprising:

A central instantiating unit which is intended for instantiating the particular device, where in each case the instantiating unit installs an individualized patient-specific or user-specific application as an encryption unit on the particular device and wherein the application stores or installs a key and a device ID in hidden form in a program memory of the device, wherein the instantiating unit stores an association at least between device ID and key in a central protected memory (to which a decryption unit also has access, for example a central registry).

An encryption unit which is installed locally on the device and is intended for generating a digital signature, wherein the signature is generated by means of encryption with the key stored by the instantiating unit, wherein the signature is generated from a signature prototype which comprises the device ID and a time stamp, and wherein the encryption unit is furthermore intended for sending at least the signature with the device ID to the server.

A decryption unit which is installed on the central server and wherein the decryption unit comprises an access module to the central protected memory and is able to access said central protected memory by means of the access module or directly, wherein the decryption unit is intended for receiving the signature sent by the device with the device ID and for reading out the particular associated key for decryption from the device ID by accessing the central protected memory in order to decrypt the received signature using the key which has been read out and from the resulting signature prototype to read out the device ID as the decryption result, wherein the decryption unit is furthermore designed to compare the decryption result with the received device ID for a match and when a match is found the decryption unit is further intended for executing an access to the repository using the device ID which has been read out.

In an example embodiment, three computer-based entities are principally provided: Firstly the mobile device, which is operated by the patient (in other words his cell phone which has been provided with the individualized application software—with the encryption unit), the patient registry which acts as central server and exchanges data over the internet or over a mobile network operator with the devices. The decryption unit is installed on the registry. In one embodiment, the instantiating unit can also be installed on the registry. In an alternative, the instantiating unit is provided as a separate entity. Furthermore, as the third entity the repository is provided as data storage, which in particular interacts with the registry in order to exchange medical patient data records. An important advantage of this architecture is the fact that no security measures and means of security from third-party suppliers are required in order to authenticate the patient on the hospital system. It is thus considerably easier for the hospitals to distribute (onto the connected devices) and to operate authentication applications.

In at least one embodiment, the following method steps are executed on the device for authentication purposes:
Firstly a signature is generated. The signature comprises at least an encrypted form of a concatenation of the device ID and a time stamp.
The signature is sent with the device ID and where applicable with a message from the device to the registry.
The signature is sent together with the device ID and where applicable a message and optionally symmetrically encrypted and instead the encryption result is sent.

In at least one embodiment, the following steps are executed on the part of the registry for authentication purposes:
The message with the signature and the device ID are received and where necessary (optionally) symmetrically decrypted.
The device ID is acquired.
With the device ID acquired, access is effected to the central protected memory in order to read out the corresponding key (associated with the device ID) in each case.
Decryption of the signature takes place using the key which has been read out.
The decrypted device ID with time stamp is read out as the decryption result. The decryption unit can now compare the decryption result with the received device ID for a match. When a match occurs the authentication process is considered successful and an access to the repository can be executed. In order to find the data records in the repository, the device ID and/or further identifying labels associated with the device ID are used.

A further embodiment is directed to a computer program product. The product comprises computer program code which is intended for carrying out all the method steps of at least one embodiment of the method described or claimed above when the computer program or the computer program code is executed on the computer. In this situation the computer program can also be stored on a machine-readable or computer-readable storage medium. An alternative provides that the computer program is read in as an executable unit over a network.

It is likewise possible that the method is divided up onto different computer entities, in particular onto an encryption unit and a decryption unit as well as onto an instantiating unit. Individual steps of the method can then be executed on the individual units (encryption and decryption unit), which means that the method and the authentication system are implemented as a distributed system. The preferred embodiment relates to a software implementation. Alternative developments provide a partly hardware-based implementation here.

The inventive embodiments described above of the method can also be designed as a computer program product with a computer program, wherein the computer is caused to carry out embodiments of the inventive method described above when the computer program is executed on the computer or on a processor of the computer.

An embodiment is further directed to a computer program with computer program code for carrying out all the method steps of at least one embodiment of the method claimed or described above when the computer program is executed on the computer. In this situation the computer program can also be stored on a machine-readable storage medium.

An embodiment is further directed to a storage medium which is intended for storing an embodiment of the computer-implemented method described above, and is computer-readable.

BRIEF DESCRIPTION OF THE DRAWINGS

In the detailed description of the figures which follows, example embodiments which are to be understood as non-restrictive are discussed with their features and further advantages with reference to the drawing. In the drawings:

FIG. 1 shows a schematic diagram of the authentication system according to an embodiment of the invention with selected entities, FIG. 2 shows a schematic representation of an instantiating unit and the communication context thereof in the context of an authentication process according to an embodiment of the invention, FIG. 3 shows a schematic representation of data and/or messages which are transmitted during data exchange with a central server and FIG. 4 shows a schematic representation of a workflow according to an example embodiment of the authentication method according to an embodiment of the invention.

The invention will be described in detail in the following with reference to the figures. Different embodiments of the invention are illustrated in the figures and the same reference characters are also used in each case for the same modules or component parts in the different figures.

DETAILED DESCRIPTION OF THE EXAMPLE EMBODIMENTS

Figure 4:
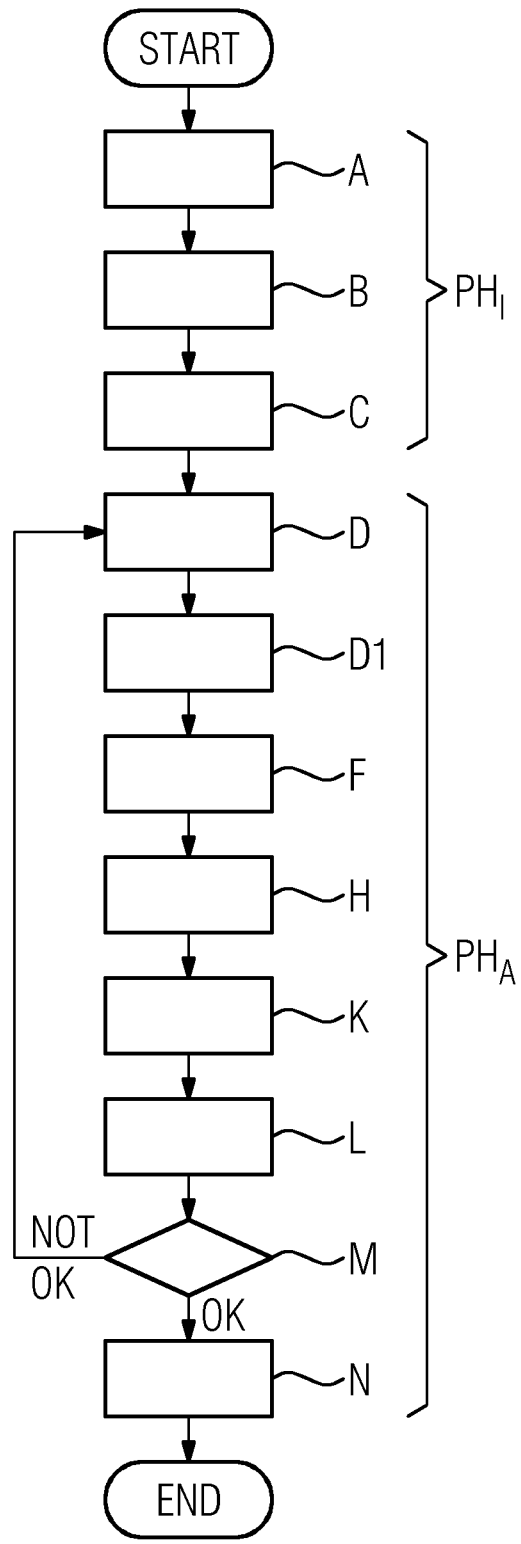

The concepts used in the context of this patent application are defined and described in detail in the following.

According to one aspect of at least one embodiment, the invention relates to an authentication system for the authentication of a particular mobile electronic device (wherein a plurality of mobile electronic devices is basically connected to the system and is to be authenticated) against a central server for the secure exchange of medical data between device and server, wherein the server for its part exchanges data with a clinical system and has access to a repository containing clinical or medical data (also including patient data), comprising:

- A central instantiating unit which is intended for instantiating the particular device, where in each case the instantiating unit installs an individualized patient-specific or user-specific application as an encryption unit on the particular device and wherein the application stores or installs a key and a device ID in hidden form in a program memory of the device, wherein the instantiating unit stores an association at least between device ID and key in a central protected memory (to which a decryption unit also has access, for example a central registry).
- An encryption unit which is installed locally on the device and is intended for generating a digital signature, wherein the signature is generated by means of encryption with the key stored by the instantiating unit, wherein the signature is generated from a signature prototype which comprises the device ID and a time stamp, and wherein the encryption unit is furthermore intended for sending at least the signature with the device ID to the server.
- A decryption unit which is installed on the central server and wherein the decryption unit comprises an access module to the central protected memory and is able to access said central protected memory by means of the access module or directly, wherein the decryption unit is intended for receiving the signature sent by the device with the device ID and for reading out the particular associated key for decryption from the device ID by accessing the central protected memory in order to decrypt the received signature using the key which has been read out and from the resulting signature prototype to read out the device ID as the decryption result, wherein the decryption unit is furthermore designed to compare the decryption result with the received device ID for a match and when a match is found the decryption unit is further intended for executing an access to the repository using the device ID which has been read out.

The authentication system basically serves to prove against a registry the identity of the patient operating his mobile electronic device, in particular his smartphone, which registry can be implemented as a server and which exchanges data with a clinical repository.

The mobile electronic device is preferably a cell phone or a smartphone or some other electronic device which is not location-dependent and in particular exchanges data with other entities over a mobile network. Alternatively, the network in question can also be a different data transmission network, for example a wireless network or the internet. The particular electronic device is associated with a patient and acts as a client of the central server and comprises at least a data memory and a program memory or a protected memory and a microprocessor module (or a CPU) for executing applications. In particular, an encryption unit is installed as an application on the device, and comprises a device ID identifying the device. In this embodiment the authentication system is designed as a client/server system. As a rule a plurality of client devices and one central server are provided, where the server can be distributed over multiple entities and comprises at least one registry.

The central server is computer-based and can also include a network of computers (for example a cloud system) or be constructed on an SOA principle (Service Oriented Architecture). The server is associated with the clinical facility and exchanges data therewith. In particular, the server exchanges data with a repository. The repository acts as a data memory for the storage of the patient's medical data and of other clinical data which is stored there on a short-term or long-term basis. The data is stored there for example (but not necessarily) as plain data (unencrypted). Access to the repository consequently needs to be protected against unauthorized access attempts.

The medical data in question is patient data, examination data, reports for a patient, examination results, findings, prescriptions or treatment instructions, emergency data records with long-term diagnoses, incompatibilities or allergies, examination or treatment appointments in different formats, comprising image data, text data or data in other formats (for example audio and/or video data).

The instantiating unit is designed as a central computer-based entity and is associated with the server. The instantiating entity in question can be a registry. In a particular embodiment the instantiating unit can not only be associated with the server but also be identical therewith, which means that the instantiating unit additionally also assumes all the functions of the server. The instantiating unit serves to instantiate the devices to be connected to the authentication system or the devices to be authenticated. The instantiating unit can be designed as a software module and/or a hardware module and preferably exchanges data with the electronic device to be authenticated and with a central protected memory, which can also be associated with the central server, over the mobile network. The instantiating unit individualizes or personalizes each electronic device by loading an individualized program (application) as a so-called "app" onto the mobile device (for example a cell phone) and installing it there.

After the app has been installed the cell phone can be identified one-to-one in the authentication system and thereby individualized. The instantiation is affected by the instantiating unit installing on the cell phone as part of the programs a key and the device ID in hidden fashion, in other words not readable, not recognizable by the device user/patient, not modifiable. The instantiating unit thus distributes specific data records and executable programs onto the devices to be authenticated in order to individualize and instantiate said devices. The instantiating unit furthermore exchanges data with a central protected memory which is associated with the server. The data exchange between instantiating unit and server can be a digital network (for example an internet-based network), a local network and where applicable also a mobile radio network.

The application in question is a software module which is installed as an executable program on the cell phone and is stored there amongst the programs in a program memory. It is important that the application is installed as an encryption unit on the patient's cell phone. The data conveyed by the application (executable file, individual key, individual device ID and possibly also other data records) is thus stored exclusively in the program memory of the cell phone and not in the data memory. The data memory of the cell phone is basically not secure and could easily be compromised or read out by unauthorized entities. Storage of the personal data which is conveyed from the instantiating unit to the device therefore takes place exclusively in hidden form in the program memory of the cell phone.

The key can be part of a symmetric encryption method and is then used concordantly by the encryption unit on the patient's cell phone and by the decryption unit on the server. This (symmetrically encrypted) implementation advantageously permits the server-driven reconstruction of the app after loss. Alternatively, an asymmetric encryption method can also be used, such as for example based on the RSA algorithm which provides a key pair consisting of a public key and a private key.

The device ID in question is a device-specific or patient-specific ID which makes it possible to identify one-to-one the device or the patient operating the device. For example, the device ID here can be the textual representation of the patient identity, in other words a string containing the patient's name together with one-to-one invariant features (date of birth, place of birth). Alternative implementations however here provide the association of a one-to-one numeric ID and/or further authentication data records.

The signature is generated locally on the cell phone by the encryption unit. When a signature is created for the first time the patient can register himself in the authentication system. All further applications are then authentication processes. The signature prototype is generated by appending the patient's name or the device ID to, or concatenating it with, a time stamp. The combined data record (with the device ID and the time stamp) is subsequently encrypted with the locally stored key. The resulting signature is then (preferably likewise initiated by the encryption unit) conveyed from the patient's local cell phone in the form of a message to the server. The message can contain requests for access to data and where applicable also further commands which can be resolved on the server side. The signature, optionally with a message, is conveyed by the cell phone over the mobile network or by a network provider to the server. The device ID is also transmitted in plain text in this situation. The signature here is the encrypted concatenation of device ID with the appended time stamp for the purpose of the authentication, which is then resolved on the server side through decryption. The signature can also comprise further invariant device-specific and/or patient-specific data records, such as for example demographic data records for the patient (place of birth, date of birth etc.) and further biometric data records for the patient (such as for example iris data, fingerprint etc.). Said further invariant data records are also stored as a copy on the central server with protected access and used for the authentication. The authentication process can thus be made yet more secure and robust against attacks. The copies of the further invariant signature data records stored on the central server or directly on the decryption unit are then compared against the decrypted signature data records for a match.

The decryption unit is computer-based and can be designed as a software module or a hardware module. The decryption unit is implemented on the central server, in particular the registry, and/or on the instantiating unit. It can however alternatively also be connected as a separate unit to the aforementioned computer-based entities over a network. The decryption unit exchanges data with the central protected memory in which an association between device ID and key is stored. Alternatively, yet further associations can be stored here in order to strengthen the authentication process yet further. For example, in addition to the aforementioned a further association with a sender address (for example mobile radio number), a device identification number, a name of the device user and possibly further identification data records can additionally be stored here.

The memory is designed as a central access-protected memory and normally associated with the central server and/or the registry. In order to access the memory the decryption unit of the server comprises either an access module or the memory is integrated directly into the server. "Protected" in this context means that a memory access can be executed only by entities and/or persons having access authorization. In the simplest case a password protection is provided here. Normally however further-reaching security measures are applied, which for example require an encryption and decryption and further-reaching authentication.

Depending on the embodiment, the signature can be produced in different ways or comprise different data records. According to a preferred embodiment, the signature prototype comprises a device-related identification record, in particular a device ID, which is associated in a one-to-one manner with the particular mobile radio device of the patient.

According to another variant of at least one embodiment of the invention, the signature prototype can again comprise user-related identification data records, for example data records which concern the identity of the particular user of the device (of the patient), such as for example features (iris data etc.) identifying the person, as already described above. Other embodiments provide further invariant data records here which are either device-specific or user-specific. It is moreover possible to incorporate a random number and/or a time stamp into the signature prototype. All the data records acquired in the signature prototype are known both to the encryption unit and also to the decryption unit, which means that the units can use the data records for encryption and decryption.

As already mentioned above, for the encryption in the context of signature generation an asymmetric encryption of the personal data by the central server is normally provided for the particular device. To this end, according to at least one embodiment of the invention the private key is stored in protected fashion ("hidden") in the device and an associated public key is stored on the server. The association of the key pair (public key, private key) is either made available by a third-party supplier or is stored in the central server.

In an alternative embodiment, the signature is generated by symmetric encryption, wherein the key to be used on both sides constitutes a secret and is therefore on the one hand stored in hidden form on the device and on the other hand must be protected on the central decryption unit. The instantiating unit generating the key must not further use or store said key. This embodiment does however have the advantage that if the app or even the device is lost the decryption unit—after further-reaching authentication of the user—is able to reproduce said app again identically.

According to a further variant of at least one embodiment of the invention, provision can be made to provide two encryptions, a first encryption using a signature method (as above: asymmetric or symmetric) and a second encryption using a symmetric method, in order to again doubly safeguard the personal data which is exchanged between server and device. The increased administrative effort is offset by the advantage that a significantly increased level of security can be achieved.

As already mentioned above, the instantiating unit is normally implemented on the central server. It is also possible that the instantiating unit is implemented as a server, which means that the instantiating unit in this case is implemented having the functionality of the server and can directly assume further functionalities of the server. In this case the computer-based units (encryption unit, registry, repository) communicate directly with the instantiating unit. This variant has the advantage that the installation effort to install the authentication system can be reduced because fewer computer-based units are required.

As already mentioned above, the mobile device in question is normally a mobile radio device. The device has a programmable execution unit with corresponding non-volatile memory chips (EEPROM, PROM, etc.). The execution unit serves to install, implement or load the encryption unit as an application. The functionality of the encryption module can thus be adapted and expanded at any time by loading a new application from the instantiating unit onto the device. An important advantage is that any commercially available device (mobile radio device) can be used, and that also no changes of any description are needed with regard to the mobile network operator (for example the mobile network operators Vodafone, Telekom etc. known in Germany). The communication between device and central server takes place as before, in other words unchanged compared with established methods, which means that the first specific authentication server is the registry or the instantiating entity which can be operated by a service provider.

In the normal application situation provision is made that the instantiating unit acts as the registry and installs patient-individual applications as the encryption unit on the device, in which the key is present in hidden form. Furthermore, the registry outputs each application via the hospital to the patient. After successful authentication, using his smartphone each patient then reaches his patient-specific entries in the repository by way of the registry.

The external service provider which operates the registry can be included in the authentication system in uncomplicated and simple fashion because said unit does not contain knowledge worth protecting. The registry thus has no knowledge of on which the device which application is loaded, neither can the registry see personal or access-protected medical patient data in plain text. Only the mobile device, in other words the patient, and the hospital repository have plain text data at their disposal. All other entities are unable to read the data and have at their disposal only data in encrypted form or data with no personal association.

In an example embodiment, three computer-based entities are principally provided: Firstly the mobile device, which is operated by the patient (in other words his cell phone which has been provided with the individualized application software—with the encryption unit), the patient registry which acts as central server and exchanges data over the internet or over a mobile network operator with the devices. The decryption unit is installed on the registry. In one embodiment, the instantiating unit can also be installed on the registry. In an alternative, the instantiating unit is provided as a separate entity. Furthermore, as the third entity the repository is provided as data storage, which in particular interacts with the registry in order to exchange medical patient data records. An important advantage of this architecture is the fact that no security measures and means of security from third-party suppliers are required in order to authenticate the patient on the hospital system. It is thus considerably easier for the hospitals to distribute (onto the connected devices) and to operate authentication applications.

According to an advantageous development of at least one embodiment of the invention, the encryption unit is implemented as an application prepared for programming the mobile device, as a so-called app. The encryption unit transmits the signature where applicable with a message and with the device ID over a standardized communication channel (for example via an internet-based hyperlink) to the server. Conversely, the server or the registry transmits the requested data to the device, which can then be displayed there on the monitor. This situation relates to a download of data from the clinical repository. In the case of the data download, in other words the transmission of medical data from the repository onto the mobile device, an asymmetric encryption of the personal data is preferred in order to provide further security measures. The transmitted data is thus transmitted only in encrypted form, which means that even if an attacker taps the message (comprising the medical data) the attacker cannot read the message. The attacker moreover receives no information as to which person (patient) this data is associated with and belongs to. The security can thereby be increased yet further.

An alternative embodiment relates to the upload of data into the repository. In this case the abovementioned steps are in each case executed on the other side (server and client interchanged), which means that the mobile device can also upload medical data records to the central memory for storage. For example, this embodiment can be advantageous if the patient has to monitor physiological parameters (for example blood pressure, heart rate, temperature, blood sugar levels etc.). After successful authentication of the patient this data can then be uploaded into the hospital repository.

In order to increase the security yet further, according to a further aspect of at least one embodiment of the invention, a time span can be preconfigured within which the authentication process must have been completed. If said preconfigured (and modifiable at any time) time span (ascertained from the difference between the decrypted time stamp from the device and the current server time on decryption) is exceeded, then an error report is output. The authentication process can be started again if necessary. Depending on the embodiment, as is known from other applications (for example bank applications) it is possible to configure that after the time span has been exceeded three times a warning notice is output to the central server and no further authentication can be performed.

According to a further aspect of at least one embodiment of the invention, it is automatically detected whether the key and/or the device ID is present unchanged, in other words in the original form, or has been corrupted. This embodiment can be combined with the previous embodiment wherein a security time span can be defined. Provided that no attack or no errored authentication can be detected, provision is made in a variant of the invention that (depending on a detected situational context) and/or in response to a confirmation signal a new installation or a reloading of the encryption unit onto the device is initiated. In this case, new individualized encryption software is therefore loaded onto the patient's mobile radio device for the purpose of authentication. According to an embodiment variant of the invention, the instantiation process can thus also be performed repeatedly.

If an attacker wished to manipulate the instantiation process without permission, then according to a further variant provision is made that it is automatically detected whether the encryption unit on the device is corrupted (detectable for example from deviations between sender address and decrypted device ID). In this case, a renewed authentication is enabled only after further-reaching analysis and possibly only after repeated authentication of the device or of the user. As a rule a further communication channel (for example in written form or using email or using some other means of secure data exchange) is provided for this purpose in order to be able to securely avert attacks and misuse.

At least one embodiment of the electronic device, as described above, is designed for use with the authentication system described above. According to at least one embodiment of the invention, an encryption application by means of which the user can register and authenticate himself is loaded onto the device. The loaded application is—as described above in the context of the description of the authentication system—stored in the program memory in hidden form and thus cannot be read, modified and/or deleted by the user.

In addition to the encryption unit, the device preferably comprises a signature unit which is intended for generating a signature in accordance with the measures described above. Messages which are sent by the device to the central server/registry are signed with the signature exclusively by way of the encryption unit. The data exchange is thus secured in all cases.

An instantiating unit is intended for use in the authentication system. In at least one embodiment, the instantiating unit can be designed as a registry and is associated with the central server. The instantiating unit serves in particular to distribute the individualized applications onto the devices and install them there. Furthermore, access to the central protected memory is affected by the instantiating unit in order to store the key and the device ID and/or the association thereof so that the decryption unit is able to decrypt messages from the device and to authenticate them on the basis of a comparison of the device IDs. The instantiating unit can be designed as a separate unit and has interfaces for exchanging data, in particular using a mobile radio interface and further network interfaces. It is as a rule computer-based.

At least one embodiment is directed to an authentication process. The method is divided into an instantiation phase and an authentication phase.

In the instantiation phase, the devices by which patients can register and authenticate themselves on the central hospital system are instantiated. In the instantiation phase, the devices are instantiated in individualized fashion with the encryption software. To this end the encryption software is installed or loaded on the device. The user of the device can register himself on the device when first using same and subsequently carry out authentication processes.

In the authentication phase, the actual authentication takes place for accessing data on the hospital system (comprising upload and download of medical data). Likewise included is any message exchange between device and hospital repository (by way of the registry).

In at least one embodiment, the following method steps are executed on the device for authentication purposes:
Firstly a signature is generated. The signature comprises at least an encrypted form of a concatenation of the device ID and a time stamp.
The signature is sent with the device ID and where applicable with a message from the device to the registry.
The signature is sent together with the device ID and where applicable a message and optionally symmetrically encrypted and instead the encryption result is sent.

In at least one embodiment, the following steps are executed on the part of the registry for authentication purposes:
The message with the signature and the device ID are received and where necessary (optionally) symmetrically decrypted.
The device ID is acquired.
With the device ID acquired, access is effected to the central protected memory in order to read out the corresponding key (associated with the device ID) in each case.
Decryption of the signature takes place using the key which has been read out.
The decrypted device ID with time stamp is read out as the decryption result. The decryption unit can now compare the decryption result with the received device ID for a match. When a match occurs the authentication process is considered successful and an access to the repository can be executed. In order to find the data records in the repository, the device ID and/or further identifying labels associated with the device ID are used.

The signature is thus included as part of each message in the manner of metadata or as an envelope.

According to an aspect of at least one embodiment of the invention, the method comprises a comparison of the decryption result with the device ID for a match. The comparison preferably comprises a comparison for the device ID being contained character by character in the signature prototype.

According to an example embodiment, the authentication process comprises a further additional comparison, namely a comparison of the times of day. If the device ID matches, meaning that the authentication process is considered successful, but the times, in other words the time stamp, do not match, then the device should be informed by way of a warning signal that the times of day need to be updated. According to an aspect of at least one embodiment of the invention, provision is however also made in this case that the deviation of the time stamps could possibly indicate the message having been compromised. The server is therefore also informed by means of a report that a compromised situation has possibly occurred here. Further analysis steps can be triggered here if necessary.

With regard to the analysis of the time stamps, a preconfigurable deviation between the time stamps can be configured. For example, it is possible to configure that a deviation of 10 minutes is still tolerable whereas deviations in excess thereof cause the output of a warning signal.

If the authentication process was able to be completed successfully, further secure channels can be opened in order to enable data exchange or direct communication between device and repository. For example, a key having limited validity can be provided for this purpose. By way of the key, data requiring authorization and protection can then be exchanged over the channel between device and repository as long as the key remains valid. In other words, following successful authentication other secure communication channels, where applicable also to other memories and/or entities, can also be opened.

Provision is normally made that the authentication process is initiated by the client (patient), in other words on the device side. Alternative embodiments however also here provide for an initiation of the authentication process on the part of the registry or the repository. This is conceivable for example if the patient is to be reminded by a corresponding message being sent from the registry and/or the repository to the device to request and/or upload data.

The data exchange between device and repository takes place exclusively in encrypted form. In this situation, either fixed device-specific keys or even device-specific keys with temporary validity are used. Even if the message is tapped, an attacker is thus not able to read the transmitted data in plain text.

Provision is normally made that a patient has a mobile radio device which he alone operates. In this case a 1:1 relationship of association is provided between user (patient) and device. Alternative embodiments do however provide that a group of patients can be addressed using one device. In this case a relationship of association of n:1 between patient and device is provided. Alternatively, it is also possible that a patient has a plurality of devices which he can use for authentication purposes. In this case the encryption unit is implemented as an application on all authentication devices. In this case a 1:n relationship of association is configured between patient and device.

A further embodiment is directed to a computer program product. The product comprises computer program code which is intended for carrying out all the method steps of at least one embodiment of the method described or claimed above when the computer program or the computer program code is executed on the computer. In this situation the computer program can also be stored on a machine-readable or computer-readable storage medium. An alternative provides that the computer program is read in as an executable unit over a network.

It is likewise possible that the method is divided up onto different computer entities, in particular onto an encryption unit and a decryption unit as well as onto an instantiating unit. Individual steps of the method can then be executed on the individual units (encryption and decryption unit), which means that the method and the authentication system are implemented as a distributed system. The preferred embodiment relates to a software implementation. Alternative developments provide a partly hardware-based implementation here.

The inventive embodiments described above of the method can also be designed as a computer program product with a computer program, wherein the computer is caused to carry out embodiments of the inventive method described above when the computer program is executed on the computer or on a processor of the computer.

An embodiment is further directed to a computer program with computer program code for carrying out all the method steps of at least one embodiment of the method claimed or described above when the computer program is executed on the computer. In this situation the computer program can also be stored on a machine-readable storage medium.

An embodiment is further directed to a storage medium which is intended for storing an embodiment of the computer-implemented method described above, and is computer-readable.

The context of an authentication process will be described in detail in the following with reference to FIG. 1. An embodiment of the invention relates to an authentication system for the authentication of many mobile electronic devices G which are operated by patients or medical staff. In the example embodiment the devices in question are cell phones or other mobile radio devices G. The mobile radio devices or smartphones G exchange data with a central server over the internet and/or over a mobile network (which is operated by any mobile radio network operator).

In the example embodiment the server is designed as a registry 10. The registry 10 is normally associated with a hospital or a hospital group, a doctor's practice or a group of doctors' practices. It can be operated by an external service provider. The registry 10 in turn exchanges data with a repository 12. Medical data records are held in the repository 12. For example examination results, findings, image data from radiological examinations, scientific studies, prescriptions, appointments etc. can be held here. The repository 12 is designed as a central and preferably also access-protected memory.

In an alternative embodiment the repository 12 can also comprise a separate storage area which is designed as protected memory. In an example embodiment the registry 10 comprises a central protected memory containing personal confidential patient data requiring authentication and having access protection. As illustrated in FIG. 1 by the arrow, the registry 10 and the repository 12 exchange data with one another. Different communication channels are conceivable here. Data exchange over a network (WLAN or LAN) is preferred. Alternatively, an internet connection over a definable version from the Internet Protocol family (for example http as an application of the TCP/IP protocol) can also be installed here.

An embodiment of the inventive architecture of the authentication system is based on mobile radio devices. In other words it is assumed that a patient or a group of patients has at its disposal a mobile radio device G. The mobile radio device G is however modified according to the invention in its device components in that it is provided with an individualized software application which is installed on the device. According to the invention, the device components are therefore also addressed differently. Sending a message N to the registry 10 for example is thus carried out exclusively by way of the installed encryption unit V.

The instantiation process mentioned above will be described in detail in the following with reference to FIG. 2. According to an example embodiment of the invention an instantiating unit I is provided which exchanges data with the devices G to be authenticated. The data connection between device G and instantiating unit I is preferably mobile radio based. Alternatively, other data transmission networks can however also be employed here.

The devices G in question are commercially available mobile radio devices of differing type and construction. The instantiating unit is a computer-based unit which is intended for instantiating the devices G and to this end installs or loads a personalized and/or device-specific application as encryption unit V onto the device G to be authenticated. This is characterized in that in FIG. 2 the arrows (which are intended to represent a data transmission) which originate from the instantiating unit I and point to the devices $G_1, G_2 \ldots G_n$ represent different versions of encryption units V, namely a first encryption unit V', a second encryption unit $V_2$ etc. In the preferred embodiment, a 1:1 association between encryption unit V and device G is provided, meaning that a first encryption unit $V_1$ is installed on the first device $G_1$, a second encryption unit $V_2$ on the second device $G_2 \ldots$ and an n-th encryption unit $V_n$ on the n-th device $G_n$. Alternatively, other associations can however also be chosen here, meaning for example that one and the same encryption unit V is distributed to a plurality of devices G and installed there (this corresponds to a 1:N association between encryption unit and device). Alternatively, it is also possible to cover other application scenarios here, meaning that a plurality of encryption units V are installed on a device G (this corresponds to an M:1 association between encryption unit and device).

Normally it is assumed that a user (normally a patient) registers on his mobile radio device by entering identification and/or authentication signals. Normally a password input, a fingerprint or other registration measures are provided here. The central server, the registry 10 and/or the instantiating unit I can thus also reach the specific patient P by way of the particular device G.

Described in the following is an individualized device-specific application which is installed as encryption unit V on the device G. However, since a specific patient normally operates a certain device, the invention also relates to the fact that the application which is installed as encryption unit V on the device G is user-specific.

The instantiation which is initiated by the central instantiating unit I transmits a software application as encryption unit V to the particular device G. The application comprises a key 40 and a one-to-one ID 50. The key is part of a cryptological method and can be designed as a symmetric key or as an asymmetric key pair 40, 40'. Both the key 40 and also the device ID 50 are stored in hidden form in a program memory 30 of the device G. This is an important feature of the invention because data to be stored is not stored in a data memory 20, as is normally the case (such as audio data, image data etc.) but in an access-protected access module of the device G, namely in the program memory 30.

The device ID 50 is an identifier for the particular device G. In other words, there is a bijective mapping between device ID 50 and device G and the device G can be identified one-to-one and addressed by way of the device ID 50. On account of the fact that the authentication data records (in particular key 40 and device ID 50) are stored in hidden form on the device G, the patient or the device user is also unable to gain access to the device ID or the key 40. He is furthermore unable to modify said data records and also unable to delete them.

After the encryption unit V has been installed locally on the device G, the user can on the first occasion subject himself to a registration process by way of the encryption unit V. The encryption unit V can subsequently be used in order to sign messages and thereby to authenticate the patient on the central registry 10 to enable accessing of the repository 12 in authenticated form to be performed.

To this end the encryption unit V generates a signature prototype SIG-UB prior to the sending of each message. The signature prototype is generated by the encryption unit V by concatenating the device ID 50 and a time stamp 60. The concatenated data record is then encrypted using the key 40.

Alternatively, the signature prototype SIG-UB can also comprise yet further authentication data records 51. The further authentication data records 51 can for example be invariant patient-specific data records (demographic data, biometric data etc.). In this case the device ID 50, the time stamp 60 and the further authentication data records 51 are linked to each other and subsequently encrypted. All messages N which are to be transmitted from the device G to the central server or to the registry 10 are signed with the signature SIG—in other words the encryption of SIG-UB.

In the context of a communication process between device G and registry 10 the registry 10 then receives the message N with the signature SIG and the device ID 50. This is illustrated in FIG. 1 by the data packet which is sent from the device G to the registry 10 which is represented by the oval "{SIG}, 50". Data exchange preferably also takes place here over the internet.

In order to be able to receive the data packet or the message N on the server side, according to an embodiment of the invention the registry 10 is expanded by a decryption unit E. The decryption unit E is installed on the registry 10 and comprises an access module Z by which access can be gained to a central protected memory MEM.

Alternatively, the decryption unit E also directly and immediately comprises the secure memory MEM. The decryption unit E is preferably designed as a software module and serves to receive the message sent, or signature SIG with the device ID 50 sent, by the device G.

Furthermore, the decryption unit E serves to perform the actual authentication process. This is done by way of the comparison of a signature prototype as the decryption result SIG-UB with the transmitted device ID 50. If the decryption result matches the device ID 50 the device G or the particular access is considered authenticated. Otherwise an error report can be output and the access is not performed.

The registry 10 resolves the transmitted message and after decryption obtains the signature prototype SIG-UB, comprising the time stamp 60 in plain text, and also the device ID 50 likewise in plain text. The decrypted data records (time stamp and device ID) are saved temporarily as the decryption result. As soon as the device ID 50 from the decryption result matches the transmitted device ID the authentication process is considered to have been executed successfully.

Alternative implementations provide yet further control measures here. For example, it is possible to analyze the time details from the time stamp 60 in order to check whether the time mark of the device G differs only by a preconfigurable difference range from the time mark of the registry 10. In other words, the registry time and the device time should differ from one another only by a preconfigurable tolerance.

Following successful authentication the registry 10 can then perform an access to the repository 12. As a rule the access is indexed by way of the device ID 50 in order to find the patient-specific and relevant data records in the repository 12 and convey them to the device G of the patient.

The data records transmitted in the context of authentication will be described in detail in the following with reference to FIG. 2. After instantiation of the device G the latter transmits message N comprising the signature SIG and the device ID 50 to the decryption unit E of the registry 10 (uppermost arrow on the left-hand side). Thereupon the decryption unit E becomes active on the server side and decrypts the result and performs the authentication process.

To this end the decryption unit E uses the device ID 50 to access the secure memory MEM in order to read out a decryption key 40'.

In an alternative development the key 40' is not stored in the repository 12 (this is also possible if the storage area is access-protected) but in a separate memory to which the registry 10 has access. The decryption key 40' is associated in a one-to-one manner with the encryption key 40 and is part of an asymmetric encryption. As a rule it involves an asymmetric key pair comprising a private key and a public key.

In this situation the private key cannot be viewed and is stored in hidden form in the program memory 30 of the device G, while the public key 40' is stored in a central memory. In this embodiment the memory (for example the repository 12) comprises an association table between device ID 50 and key 40, 40'. After the associated decryption key 40' has been released in each case it is forwarded to the decryption unit E. Thereupon the decryption unit E can decrypt the signature SIG, resulting in the signature prototype SIG-UB, in order to then perform the authentication process by comparison (as already described above).

On successful authentication an access can again be performed to the repository 12 in order to read in and preferably to encrypt in encrypted form (normally with the public key 40') the specifically requested data record and transmit it via the registry 10 to the device G. The encrypted data is identified in FIG. 2 by the label "ENC (DATA)".

The process described above relates to a data download of medical data records onto the device G. The authentication process according to an embodiment of the invention can however similarly be used for a data upload in which the patient uses his device G to send data records to the central repository 12 for storage. For example, the data records concerned here can be current values measured for the patient's blood pressure, blood glucose level, temperature etc.

In a further advantageous and also example embodiment, instead of the device ID 50 a patient number is saved in hidden form into the program memory 30 on the device G and transmitted as part of the message N to the registry 10 for authentication purposes. With regard to the key likewise stored in the program memory 30, this is a secret key of the patient (private key). As part of each communication or each data request the encryption unit V then sends the signed concatenation of patient number and time stamp 60 (with both the patient number and therefore also the time stamp 60 for example being post-encrypted using a symmetric encryption method) to the registry 10. The time stamp 60 is thus transmitted encrypted as part of the signature SIG with regard to each message in order to have a variable portion of the message which has to be resolved by the server or the decryption unit E in order to be able to better avert attacks by unauthorized persons—who could use a copy of an earlier SIG.

As an important advantage of an embodiment of the invention it can be stated that no changes to the device G are required. In other words, it is simply necessary to install the encryption application V on the device G. There are no further requirements on the device G, which means that commercially available mobile radio devices can also be used here. Furthermore, it is also the case that no specific precautions are necessary with regard to the mobile network operator.

A further advantage which can increase the security of the authentication system according to an embodiment of the invention is the fact that no unencrypted medical data records are transmitted between device G and repository 12. Only the patient as the client of the device G and the hospital repository 12 have data records in plain text at their disposal. The data records exchanged are transmitted exclusively in encrypted form.

Provision is preferably made that the public key is likewise stored in a central protected memory MEM which is associated with the decryption unit E and thus the registry 10. Normally the key is maintained in the registry 10. The data which has been requested by the device G and following a successful authentication process is to be sent from the repository 12 to the device G is encrypted with the public key of the device G or of the requesting patient P. To this end the repository 12 accesses the public key of the registry 10. As soon as the data is then received on the device the encryption unit V can be designed to decrypt the encrypted data with the secret or private key.

An alternative embodiment provides for the use of a further key pair in order to yet further increase the security. Here again the method in question for encrypting the personal data can be asymmetric or symmetric.

A workflow of an authentication process according to an example embodiment will be described in detail in the following with reference to FIG. 4.

After the start of the authentication process the method is divided into an instantiation phase and an authentication phase. Successful completion of the instantiation is necessary in order to carry out the authentication phase.

The instantiation relates to the instantiation of the devices G. This is indicated in FIG. 4 by the method step A. To effect instantiation, an encryption unit V is installed on the device G as a software application which stores a device ID or a patient ID 50 and a key 40 in hidden form in the program memory 30 of the device. The application serves to encrypt and decrypt medical data records which are exchanged with the repository 12. The installation process is indicated by the reference character B in FIG. 4.

The client or patient, or user, can subsequently register himself on his device G. This is indicated by the method step C.

Firstly, all the devices G must be instantiated in order to be available later for an authentication process.

In the authentication phase a patient can authenticate and identify himself to the central registry 10 by means of his mobile radio device G.

To this end a signature is generated in method step D. The signature prototype SIG-UB is composed of a device ID or patient ID 50 and a time stamp 60. Both data records form the signature prototype SIG-UB which is encrypted with a key 40 and thus forms the signature SIG.

In step D1, a message N with signature SIG and device ID 50 is sent to the registry 10.

In method step F, the message N is received on the server side on the registry 10.

In step H, the transmitted device ID 50 is detected. Described in the following is the embodiment in which the device ID 50 is transmitted. As already mentioned above, it is however also possible to transmit a patient identification number, which identifies the particular patient one-to-one, instead of the device ID 50.

In method step K, access is effected to the central protected memory MEM which is associated with the registry 10. The access serves to read out the decryption key 40' which is associated with the device ID 50. The decryption key 40 is used for decryption of the received message N. In the following method step L the message N with the received signature SIG is decrypted using the key 40'. In this situation a signature prototype SIG-UB is generated as the decryption result and compared for a match with the device ID 50 which has been read out.

The comparison of the decryption result with the device ID 50 takes place in method step M.

When a match is found, in step N an access to the repository 12 is executed using the device ID 50 which has been read out in order to read out the particular medical data. The method can terminate thereafter.

As illustrated in FIG. 4, access to the repository 12 takes place only if the authentication was successful. This is identified by the oval bearing the designation "OK". Otherwise the method can either terminate immediately or the authentication process is repeated, which is represented in FIG. 4 by the upward pointing arrow, meaning that the method starts again at method step D.

Basically, two different embodiments which provide a different encryption system are possible: A symmetric method or an asymmetric method. Alternatively, combinations can also be used. In symmetric encryption the key 40 is an identical match with the key 40'. In asymmetric encryption the key 40 is preferably a private key and the key 40' the corresponding public key of the key pair.

To summarize, an embodiment of the invention can be described as having a patient authentication, the architecture of which is based on a conventional mobile radio device (cell phone) which exchanges data with a central registry 10 and an instantiating unit I. The instantiating unit I installs individualized apps on the cell phone of the patient. The authentication data records such as keys 40, 40' and device ID 50 are maintained both locally on the cell phone and also in a central protected memory MEM of the registry 10. Software applications which execute the authentication process after transmission of a message N from device G to registry 10 are installed (encryption unit V and decryption unit E) both on the cell phone and also in the central registry 10. The medical data records are located in the hospital repository 12 and are also available for the mobile device G following successful authentication by way of the registry 10.

The invention is however not restricted to the example embodiments described above but can also be implemented in other application contexts. It is thus possible that the steps of the method are not all executed on the same computer-based unit but on different units, such as for example on the device G, on the registry 10 and/or on the instantiating unit I. The sequence of the steps can in part also be modified. It is likewise possible to further expand the authentication system described above, and make available identity checks on the part of the device G, such that the identity of the particular patient can also be checked locally on the device G (for example through optical image control, checking of biometric data or confirmation of demographic data etc.). This embodiment is particularly valuable in medical emergency situations in which the patient is possibly no longer conscious and an assisting person is thus placed in the position of performing the authentication process on behalf of the patient and authenticating said patient locally in order to request data records relevant to the emergency from the repository 12 (for example long-term diagnoses, incompatibilities or allergies etc.). Other differences likewise fall within the scope of the invention, such that the scope of protection is determined solely by the patent claims listed in the following.

The invention claimed is:

1. An authentication system for authentication of a respective mobile device from a plurality of mobile devices against a server for secure exchange of medical data between the respective mobile device and the server, wherein the server is configured to access a repository containing the medical data, the system comprising:
   the server, wherein the server includes memory storing computer-readable instructions; and one or more processors configured to execute the computer-readable instructions such that the one or more processors are configured to
     receive a request from one of the plurality of mobile devices for an individualized device-specific application,
     respectively instantiate one of the plurality of mobile devices by installing the individualized device-specific application as an encryption application on the respective mobile device, wherein the encryption application is configured to store a key and a device ID in hidden form in a program memory of the respective mobile device, and
     store an association between device ID and key in a central protected memory of the respective mobile device;
   the encryption application being installed locally on the respective mobile device and configured to generate a digital signature, wherein the digital signature is encrypted using the key stored by the server and is generated from a signature prototype, comprising at least the device ID and a time stamp, and wherein the encryption application is furthermore configured to send at least the digital signature and the device ID to the server; and wherein the server includes
   a decryption application, installed on the server and including an access module to the central protected memory, the decryption application including computer-readable instructions such that the one or more processors are configured to receive the digital signature sent by the respective mobile device with the device ID and configured to read out the respective associated key for decryption from the device ID by accessing the central protected memory in order to decrypt the received signature using the key and from the signature prototype to read out the device ID as a decryption result, wherein the decryption application is further configured to compare the decryption result with the device ID for a match and when a match is found, the decryption application is further configured to execute an access to the repository using the device ID which has been read out.

2. The authentication system of claim 1, wherein the signature prototype comprises a device-related identification data record.

3. The authentication system of claim 1, wherein the signature prototype comprises a user-related identification data record.

4. The authentication system of claim 1, wherein the signature prototype comprises at least one of, known to the encryption application and the decryption application,
   at least one of invariant device-specific and user-specific authentication data records, and
   at least one of a random number and a time stamp.

5. The authentication system of claim 1, wherein the one or more processors are configured to store a private key in protected fashion in the respective mobile device and wherein a public key is stored on the server for at least one of each of the plurality of mobile device and each device ID.

6. The authentication system of claim 1, wherein the one or more processors are implemented on the server.

7. The authentication system of claim 1, wherein the respective mobile device is a mobile computer-based electronic device with memory storing computer-readable instructions; and one or more processors configured to execute the computer-readable instructions.

8. The authentication system of claim 1, wherein the encryption application is implemented as software application prepared for programming the respective mobile device and wherein the encryption application is configured to transmit the signature with the device ID over a standardized communication channel identifiable in plain text to the server.

9. The authentication system of claim 1, wherein a time span is preconfigurable within which the authentication process must have been completed and wherein, if the time span is exceeded, an error report is output and the authentication process is startable again or a reinstallation becomes necessary.

10. The authentication system of claim 1, wherein, in order where necessary to initiate a reinstallation of the encryption application on the respective mobile device, at least one of
it is automatically detectable whether at least one of the key and the device ID is corrupted, and
it is automatically detectable whether a preconfigured security time span is exceeded.

11. The authentication system of claim 1, wherein the data exchange between respective mobile device and server comprises at least one of a data upload and a data download.

12. A mobile electronic device comprising:
an encryption application, installed locally on the mobile electronic device, configured to generate a digital signature, the mobile electronic device being useable in the authentication system of claim 1, wherein the signature is encrypted with the key stored by the server and is generated from a signature prototype including at least of the device ID and a time stamp, and wherein the encryption application is furthermore configured to send at least the signature and additionally the device ID to the server.

13. A server comprising:
memory storing computer-readable instructions; and one or more processors configured to execute the computer-readable instructions such that the one or more processors are configured
a decryption application stored in a memory, the server being useable in the authentication system of claim 1, the decryption application comprising an access module to the memory, the decryption application being configured to receive the signature sent by the respective mobile device with the device ID and being configured to read out the key for decryption from the device ID by accessing the central protected memory in order to decrypt the received signature using the key and from the resulting signature prototype to read out the device ID as the decryption result, wherein the decryption application is further configured to compare the decryption result with the device ID for a match and when a match is found, the decryption application is configured to execute an access to the repository using the device ID which has been read out.

14. A method for authentication of a respective mobile device from a plurality of mobile devices against a server for secure exchange of medical data between the respective mobile device and the server, the server being configured to access a repository containing the medical data, comprising:
instantiating the respective one of the plurality of mobile devices, wherein an individualized device-specific application is installed as an encryption application on the respective mobile device and wherein a key and a device ID are stored in hidden form in a program memory of the respective mobile device, and wherein an association between device ID and key is stored in a central protected memory;
generating a digital signature locally on the respective mobile device, wherein the signature is encrypted with the key stored by the server and is generated from a signature prototype comprising at least the device ID and a time stamp;
sending at least the signature with the device ID to the server;
receiving the signature with the device ID sent by the respective mobile device on the server;
detecting the device ID;
accessing the central protected memory with the detected device ID in order to read out the key for the decryption;
decrypting the received signature using the key and generating a decryption result, including a device ID which has been read out;
comparing the decryption result with the device ID for a match; and
accessing the repository, when a match is found, using the device ID read out to the repository.

15. A non-transitory computer program product, wherein the computer program product comprises a computer program, stored on a data medium or in a memory of a computer and including commands readable by the computer, to carry out the method of claim 14 when the commands are executed on the computer.

16. The method of claim 14, wherein the signature prototype comprises a device-related identification data record.

17. The authentication system of claim 7, wherein the respective mobile device is a smartphone.

18. A non-transitory computer program product, wherein the computer program product comprises a computer program, stored on a data medium or in a memory of a computer and including commands readable by the computer, to carry out the method of claim 16 when the commands are executed on the computer.

19. The method of claim 14, wherein the signature prototype comprises a user-related identification data record.

20. A non-transitory computer program product, wherein the computer program product comprises a computer program, stored on a data medium or in a memory of a computer and including commands readable by the computer, to carry out the method of claim 19 when the commands are executed on the computer.

21. The authentication system of claim 2, wherein the signature prototype comprises at least one of, known to the encryption application and the decryption application,
at least one of invariant device-specific and user-specific authentication data records, and
at least one of a random number and a time stamp.

22. The authentication system of claim 3, wherein the signature prototype comprises at least one of, known to the encryption application and the decryption application, at least one of invariant device-specific and user-specific authentication data records, and at least one of a random number and a time stamp.

23. An authentication system for authentication of a respective mobile device from a plurality of mobile devices against a server for secure exchange of medical data between the respective mobile device and the server, wherein the server is configured to access a repository containing the medical data, comprising:

the server, to receive a request for an individualized device-specific application from one of the plurality of mobile devices and instantiate a respective one of the plurality of mobile devices, wherein the server is configured to install the individualized device-specific application as an encryption application on the respective mobile device and wherein the individualized device-specific application is configured to store a key and a device ID in hidden form in a program memory of the respective mobile device, wherein the server is configured to store an association between device ID and key in a central protected memory; and a decryption application, installed on the server and including an access module to the central protected memory, configured to receive a digital signature from the respective mobile device, the digital signature being previously encrypted using the key stored by the server and generated from a signature prototype and the digital signature including at least the device ID and a time stamp, and configured to read out the respective associated key for decryption from the device ID by accessing the central protected memory in order to decrypt the received signature using the key and from the signature prototype to read out the device ID as a decryption result, wherein the decryption application is further configured to compare the decryption result with the device ID for a match and when a match is found, the decryption application is further configured to execute an access to the repository using the device ID which has been read out.

24. The authentication system of claim 23, wherein the signature prototype comprises a device-related identification data record.

25. The authentication system of claim 23, wherein the signature prototype comprises a user-related identification data record.

26. The authentication system of claim 23, wherein the signature prototype comprises at least one of, known to the encryption application and the decryption application, at least one of invariant device-specific and user-specific authentication data records, and at least one of a random number and a time stamp.

27. The authentication system of claim 23, wherein the server is configured to store a private key in protected fashion in the respective mobile device and wherein a public key is stored on the server for at least one of each of the plurality of mobile device and each device ID.

28. A method for authentication of a respective mobile device from a plurality of mobile devices against a server for secure exchange of medical data between the respective mobile device and the server, the server being configured to access a repository containing the medical data, comprising:

instantiating the respective one of the plurality of mobile devices, wherein an individualized device-specific application is installed as an encryption application on the respective mobile device and wherein a key and a device ID are stored in hidden form in a program memory of the respective mobile device, and wherein an association between device ID and key is stored in a central protected memory;

receiving a digital signature with the device ID from the respective mobile device on the server, the digital signature being previously encrypted with the key stored by the server and generated from a signature prototype including at least the device ID and a time stamp;

detecting the device ID;

accessing the central protected memory with the detected device ID in order to read out the key for the decryption;

decrypting the received signature using the key and generating a decryption result, including a device ID which has been read out;

comparing the decryption result with the device ID for a match; and accessing the repository, when a match is found, using the device ID read out to the repository.

29. A non-transitory computer program product, wherein the computer program product comprises a computer program, stored on a data medium or in a memory of a computer and including commands readable by the computer, to carry out the method of claim 28 when the commands are executed on the computer.

* * * * *